US009427204B2

(12) United States Patent
Graumann

(10) Patent No.: US 9,427,204 B2
(45) Date of Patent: Aug. 30, 2016

(54) METHOD AND C-ARM SYSTEM FOR ACQUISITION OF A TWO-DIMENSIONAL, X-RAY PROJECTION IMAGE

(71) Applicant: Rainer Graumann, Hoechstadt (DE)

(72) Inventor: Rainer Graumann, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 682 days.

(21) Appl. No.: 13/768,208

(22) Filed: Feb. 15, 2013

(65) Prior Publication Data

US 2013/0216023 A1     Aug. 22, 2013

(30) Foreign Application Priority Data

Feb. 16, 2012  (DE) .................. 10 2012 202 360

(51) Int. Cl.
| | | |
|---|---|---|
| *A61B 6/00* | (2006.01) | |
| *H04N 5/32* | (2006.01) | |
| *H05G 1/60* | (2006.01) | |
| *G06K 9/32* | (2006.01) | |
| *G06T 5/50* | (2006.01) | |
| *G06K 9/20* | (2006.01) | |

(52) U.S. Cl.
CPC ........... *A61B 6/5241* (2013.01); *A61B 6/4452* (2013.01); *A61B 6/5235* (2013.01); *G06K 9/32* (2013.01); *A61B 6/4405* (2013.01); *A61B 6/4441* (2013.01); *A61B 6/545* (2013.01); *G06K 2009/2045* (2013.01); *G06T 5/50* (2013.01); *H04N 5/32* (2013.01); *H05G 1/60* (2013.01)

(58) Field of Classification Search
CPC .... A61B 6/00; A61B 6/4021; A61B 6/4028; A61B 6/44; A61B 6/4405; A61B 6/4429; A61B 6/4435; A61B 6/4441; A61B 6/4452; A61B 6/52; A61B 6/5229; A61B 6/5235; A61B 6/5241; A61B 6/54; A61B 6/545; A61B 6/587; H04N 5/32; H04N 5/23229; H04N 5/23238; H04N 5/2356; G06T 5/00; G06T 5/50; H05G 1/60; G06K 9/32; G06K 2009/2045
USPC ....... 378/11, 13, 55, 62, 91, 98, 98.8, 98.12, 378/189, 193, 197, 198, 204, 205, 210, 378/901; 382/128, 131, 216, 275, 276, 284, 382/293, 294
See application file for complete search history.

(56) References Cited

U.S. PATENT DOCUMENTS

| | | | | |
|---|---|---|---|---|
| 5,432,834 | A * | 7/1995 | Gershman | .................... 378/196 |
| 7,093,976 | B2 | 8/2006 | Fadler et al. | |
| 2008/0056451 | A1 * | 3/2008 | Gotoh | ........................... 378/197 |
| 2010/0166146 | A1 | 7/2010 | Tomisaki | |
| 2011/0188726 | A1 | 8/2011 | Nathaniel et al. | |

* cited by examiner

*Primary Examiner* — Anastasia Midkiff
(74) *Attorney, Agent, or Firm* — Schiff Hardin LLP

(57) ABSTRACT

In a C-arm system and a method for image acquisition of an x-ray projection image, wherein the projection region of the subject that is to be images is larger than the maximum projection region covered by a stationary x-ray beam, and to generate a complete exposure of the entire projection region to be imaged, at least two individual projection exposures are generated and combined. The generation of the at least two individual exposures takes place with a focus that is stationary relative to the subject and with a modified spatial angle of the emitted x-ray beam.

11 Claims, 4 Drawing Sheets

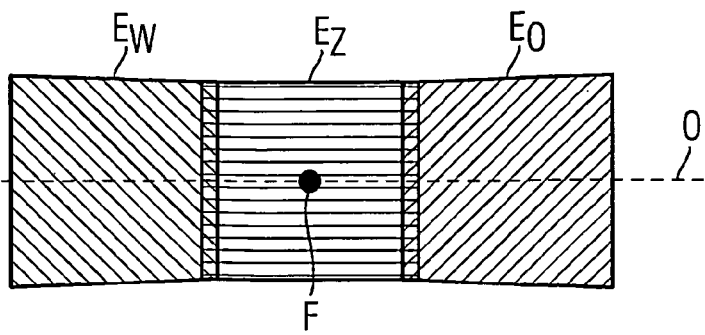
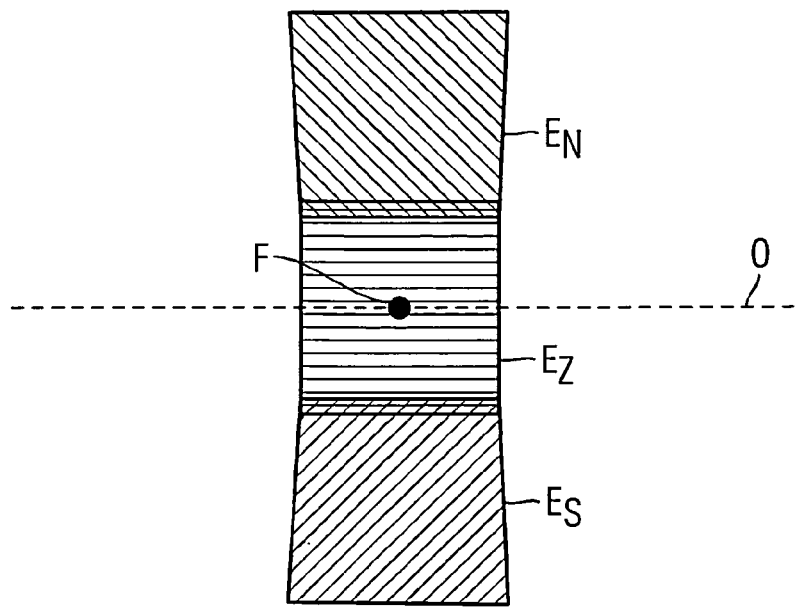
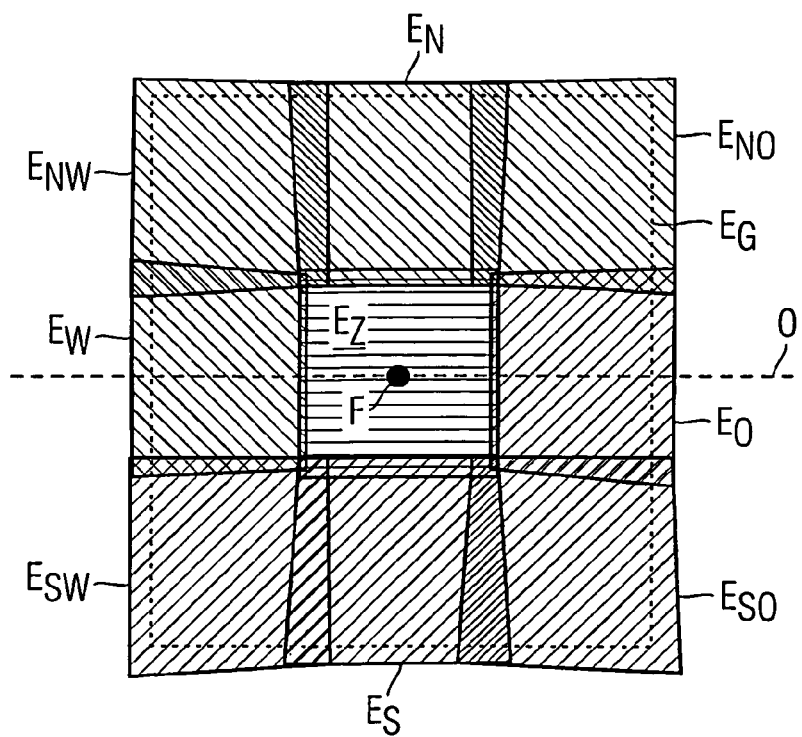

METHOD AND C-ARM SYSTEM FOR ACQUISITION OF A TWO-DIMENSIONAL, X-RAY PROJECTION IMAGE

BACKGROUND OF THE INVENTION

1. Field of the Invention

The invention concerns a method for parallax-free image acquisition of a two-dimensional, x-ray projection image of a predetermined projection region of a subject (in particular a patient) with a C-arm system, wherein the projection region of the subject that is to be imaged is larger than the maximum projection region between focus and detector that is covered by a stationary x-ray beam, and wherein at least two such individual rejection exposures are created and combined to generate a complete exposure of the entire projection region of the subject that is to be imaged.

Furthermore, the invention concerns a C-arm x-ray system, in particular mobile C-arm system having a C-arm that can be rotated automatically and moved in translation, with a radiation source with a focus being mounted at one end of the C-arm and a flat panel detector being mounted at the other end, wherein a control and computer system is connected with the C-arm system for automatic control of the C-arm and for image generation from acquired detector data.

2. Description of the Prior Art

C-arm systems as well as methods to generate projection exposures of the above general type are known and are frequently used in clinical applications for diagnosis and therapy support. The size of the flat panel detector that is used is limited, in particular in the mobile embodiment of such systems. For example, flat panel detectors with approximately 9-inch diagonals are presently used, from which results (dependent on the acquisition geometry) a projected field of view (image field) with less than 20 cm diagonals at or in the patient. Although this is sufficient in order to image individual smaller organs or bones, neither a complete lung exposure nor a complete pelvis exposure can be generated.

Furthermore, to solve this problem it is known in practice to acquire multiple x-ray images in the same acquisition geometry but with different perspectives (thus with a C-arm shifted in parallel), and assemble these individual exposures into a complete image. It is inherent to C-arm systems that, due to their structural support, the C-arm can execute only orbital rotations, rotations around a horizontal axis through the orbital plane, linear translations and what is known as a swivel motion (rotation around the vertical C-arm column). The multiple individual exposures acquired to cover a larger region to be imaged are normally executed by linear displacement of the acquisition system. However, the disadvantage hereby results that the complete exposure that is created from this procedure is a combination of individual images that were projected with the same (relatively small) projection angle but from different starting points (thus different focus positions), and therefore the assembled image does not give the natural impression of a single exposure with a large projection angle. A parallax error is thus created.

SUMMARY OF THE INVENTION

An object of the invention is to provide a method to generate a composite, complete exposure from multiple individual exposures that is free of parallax errors, and accordingly to also provide a C-arm system that executes such a method largely automatically.

The invention is based on the insight that this object can be achieved by the C-arm not being moved further horizontally between the individual acquisitions, but rather by rotating the x-ray beam around the location of the x-ray focus as a pivot point. The exposures are thereby generated without parallax error and can be placed immediately one after another in the assembled, composing image. For example, the rotation around the pivot point can be generated by a combination of height and length displacement, as well as an orbital rotation, or by height displacement, swivel and angulation.

The method according to the invention thus constitutes an improvement over known methods for image acquisition of a two-dimensional, x-ray projection image of a predetermined projection region of a subject (in particular a patient) with a C-arm system, wherein the projection region of the subject that is to be imaged is larger than the maximum projection region between the focus and the detector that is covered by a stationary x-ray beam, wherein at least two individual projection exposures are generated and combined to produce a complete exposure of the entire projection region of the subject that is to be imaged. For the improvement according to the invention, the generation of the at least two individual exposures takes place with a stationary focus relative to the subject and with a modified solid angle of the x-ray beam.

The C-arm can be moved between the individual acquisitions such that, given a stationary focus, the detector is pivoted on a spherical surface with the focus as a center point.

Furthermore, the C-arm can also be moved between the individual acquisitions such that the focus is always located at the same position that is stationary relative to the subject, at least a the acquisition point in time. This means that the position of the focus does not need to be stationary at every point in time of the movement; rather, a constant position of the focus must be present only at the end of the movement. The control of such movements is thereby significantly simplified.

The movement of the C-arm can take place so that a combined rotation around the middle point of the C-arm in the orbital plane spanned by the C-arm and translation in the orbital plane spanned by the C-arm is executed between at least two individual acquisitions with the C-arm system.

Alternatively, a combined rotation around the middle point of the C-arm orthogonal to an orbital plane spanned by the C-arm and a translation orthogonal to the orbital plane spanned by the C-arm can be executed between at least two individual exposures with the C-arm system.

Furthermore, at least three individual acquisitions can also be executed, wherein a combined rotation around the center point of the C-arm orthogonal to an orbital plane spanned by the C-arm and a translation orthogonal to the orbital plane spanned by the C-arm, and a combined rotation around the middle point of the C-arm in the orbital plane spanned by the C-arm and a translation in the orbital plane spanned by the C-arm, are executed between the acquisitions.

Furthermore, in the combination of the individual exposures into a complete exposure it is advantageous for at least some of the individual exposures to be spatially transformed such that a complete exposure results in a common projection plane. Overall, the exact impression of a single projected image that has a significantly larger projection angle (that corresponds to the sum of the projection angles used in total, apart from possible overlaps) is thereby generated by transformation of the image data into the complete image.

Operation is particularly facilitated when, apart from a manually adjusted central projection, a central individual exposure and at least two individual exposures situated around the central projection are generated automatically. For example, a number of individual exposures can be created automatically that previously had to be acquired manually.

Furthermore, starting from a manually set central projection, the central individual exposure and eight individual exposures of the examination subject situated around the central projection can be generated and combined into a complete exposure. The complete image is therefore generated from additional individual images arranged around the central individual image, such that the enlargement of the projection area takes place in the complete projection plane of the central individual image.

A further simplification of the method can be achieved by establishing two vertices (for example diagonal vertices of a rectangle), three vertices (for example the vertices of a triangle or three circumferential points of an ellipse or a circle), or four vertices (for example of a trapezoid) of a projection region to be reproduced, by manually approaching the vertices, and then the entire projection region that is thereby defined is acquired by a number of automatically created individual exposures. Before approaching these vertices, the desired geometry of the region to be projected can be changed. Moreover, the central projection plane in which the composite projection should be presented can additionally be defined in the same manner.

In a further embodiment of the method according to the invention, in addition to a central individual image, a number of adjacently arranged parts (thus for example narrow stripes) of the individual images can be combined to generate the complete exposure. Naturally, more individual exposures may possibly be necessary for this than given the use of the entire projection area of the individual images.

In addition to the method according to the invention, the invention encompasses the improvement of a C-arm system with a C-arm that can be rotated automatically and that can be moved in translation. At one end of the C-arm a radiation source with a focus is mounted and a flat panel detector is mounted on the other end. A control and computer system is connected with the C-arm system, for automatic control of the C-arm and image generation from acquired detector data. For the improvement, at least one computer program is stored in the control and computer system, this computer program being executed during operation and causing the steps of the method according to the invention described above to be implemented.

In an embodiment of this C-arm system, the C-arm can be connected with a movement device that has a sensor technology that detects manual movement forces (impulses) at the C-arm and (given selection of a predetermined movement mode) rotates in combination and linearly moves the C-arm corresponding to the direction of a detected movement impulse, such that the focus is held stationary but a movement of the detector takes place in the direction of the detected movement impulse.

Alternatively, the C-arm can be connected with a movement device that has a sensor technology that automatically supplements a manually executed rotation movement at the C-arm with translation movements such that the focus is kept stationary.

In both of the last cited embodiments, it is ensured that, given a manual movement of the C-arm, possibly with simultaneous viewing of a current projection, the focus is positioned stationary so that the exposures acquired in such a manner are generated without parallax error. Within the scope of the invention, the possibility additionally exists to transform the acquired projection exposures immediately (online) during the panning of the C-arm around the stationary focus position so that they always correspond to a projection in a predetermined projection plane.

BRIEF DESCRIPTION OF THE DRAWINGS

FIG. 3 schematically shows three projected individual images along the orbital plane with stationary focus.

FIG. 4 schematically shows three projected individual images orthogonal to the orbital plane with stationary focus.

FIG. 5 schematically shows eight individual images placed around a central individual image with stationary focus;

DESCRIPTION OF THE PREFERRED EMBODIMENTS

Figure 1:
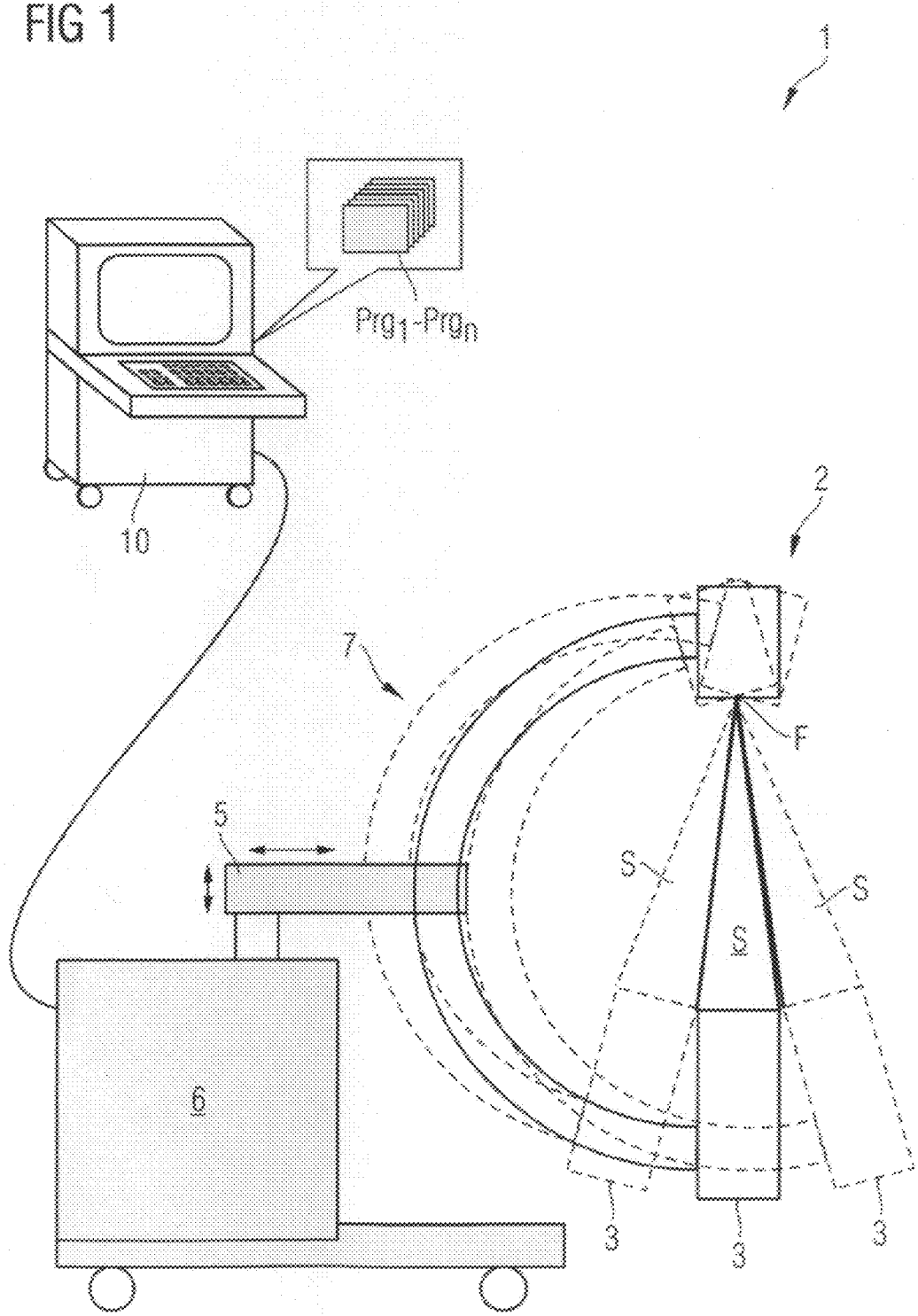
FIG. 1 shows a mobile C-arm system in side view, in which a rotation along the orbital plane around the stationary x-ray focus is generated via combined length and height displacement and orbital rotation.

In the following, the invention is described in detail using preferred exemplary embodiments with the aid of figures, wherein only the features necessary to comprehend the invention are shown. The following reference characters are used: 1: C-arm system; 2: x-ray tube; 3: detector; 5: support arm; 6: housing; 7: C-arm; 8: patient bed; 10: control and computer system; EG: complete image; $E_N$, $E_{NO}$, $E_{NW}$, $E_O$, $E_S$, $E_{SO}$, $E_{SW}$, $E_W$, $E_Z$: individual image; F: focus; O: orbital plane; P: patient; Prg1-Prgn: computer programs; S: beam.

To explain the invention, FIG. 1 shows in side view a mobile C-arm system 1 borne on rollers, having a housing 6 with a support arm 5 that can be adjusted horizontally and vertically corresponding to the indicated arrows, on which support arm 5 is mounted in turn the C-arm 7 of the system with the x-ray tube 2 and the detector 3 mounted opposite each other at the respective ends of the C-arm 7. The C-arm 7 is articulated so as to be able to rotate around the longitudinal axis of the support arm 5, but can also be rotated in a known manner within the orbital plane spanned by the C-arm. The rotation axis is orthogonal to the orbital plane and intersects the central ray of the beam emanating from the x-ray tube 2 (more precisely from the focus F).

Three positions of the C-arm 7 are depicted in the shown presentation, wherein here the rotation of the C-arm 7 in the orbital plane was coupled with transversal movements of said C-arm 7 such that the focus F was respectively held stationary in the same position in the three settings. The sum of the beam S that is generated with this accordingly spans a complete beam whose common intersection point is formed by the focus F.

Individual images are respectively acquired in this way at the three shown positions of the C-arm, which individual images were then generated without parallax error—thus with a common focus—and thus can be combined into a complete image.

For example, if three individual exposures are created in this way, an image thus results as it is shown in FIG. 3. This shows a schematic view of the projected individual images consisting of the central individual image $E_Z$ and the two individual images $E_O$ and $E_W$ adjacent to the east and west.

Figure 2:
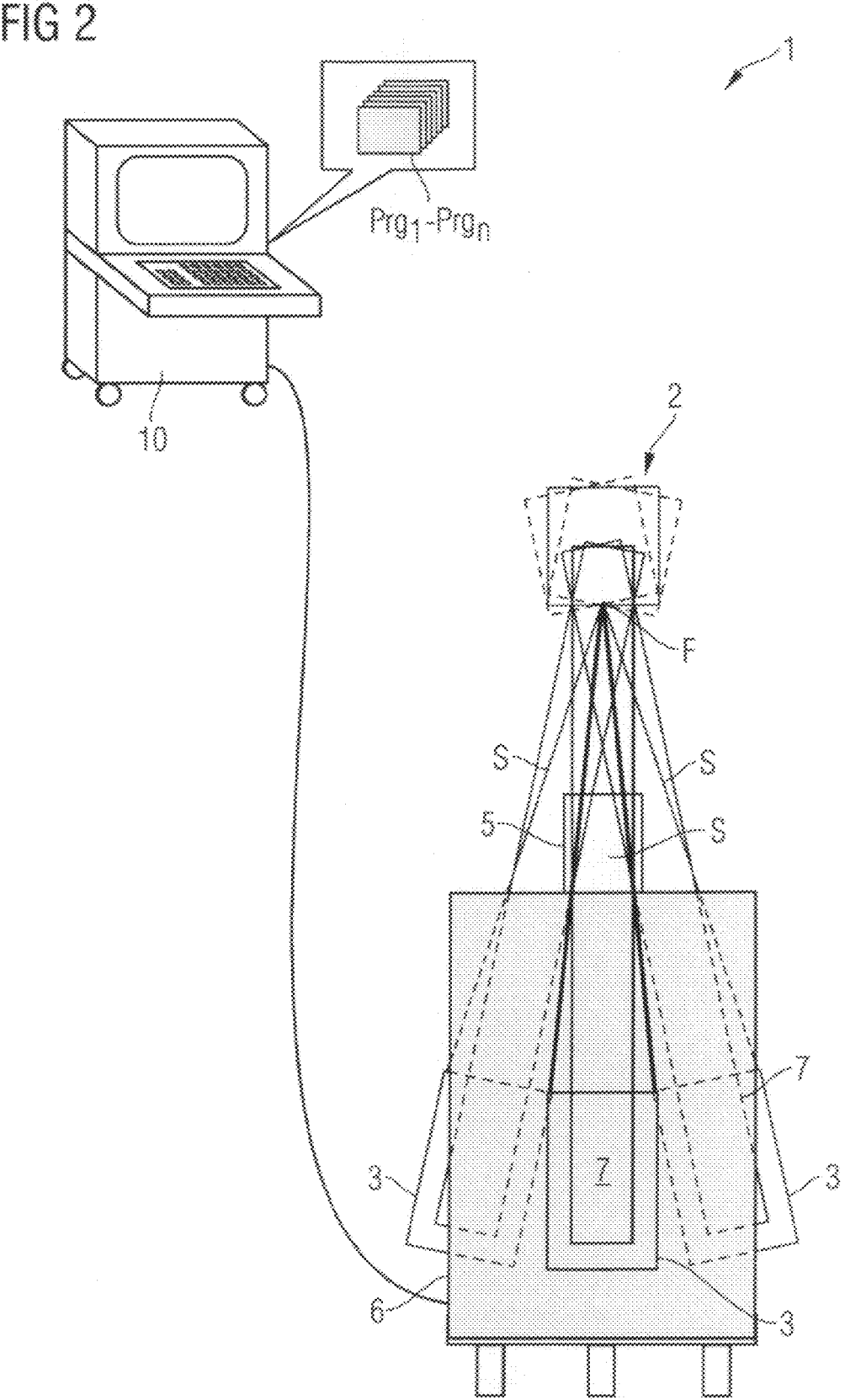
FIG. 2 shows a mobile C-arm system in front view, in which a rotation orthogonal to the orbital plane around the stationary x-ray focus is generated via combined height and transversal shift (swivel) and angular rotation.

An additional variant of the movement of the C-arm according to the invention, with focus F that is stationary and spatially identical at least at the point in time of acquisition, is shown in FIG. 2. Here a mobile C-arm system 1 is shown in frontal view, wherein the C-arm 7 is simultaneously moved via a combined height and transversal displacement (swivel) and angular rotation while the x-ray focus is located at the identical location at least during the acquisition point in time of the three shown projections. As shown in FIG. 4, three projected individual images $E_Z$, $E_S$ and $E_N$ are accordingly acquired orthogonal to the orbital plane with stationary focus and can be combined according to the invention.

FIG. 5 additionally shows the result of an acquisition sequence in which eight additional individual images $E_N$, $E_{NO}$, $E_O$, $E_{SO}$, $E_S$, $E_{SW}$, $E_W$ and $E_{NW}$ are grouped around a central individual image $E_Z$ and can be combined into a complete image $E_G$ with projection angles enlarged in all four primary directions.

The implementation of the method according to the invention in the C-arm systems 1 shown in FIGS. 1 and 2 is executed by the control of the system with the aid of the control and computer system 10 and the computer programs $Prg_1$-$Prg_n$ that are stored on said control and computer system 10. It is noted that, in the case of mobile C-arm systems, this computer system 10 is most often normally integrated into the housing, and is shown separately in FIGS. 1 and 2 only for special clarification.

Figure 6:
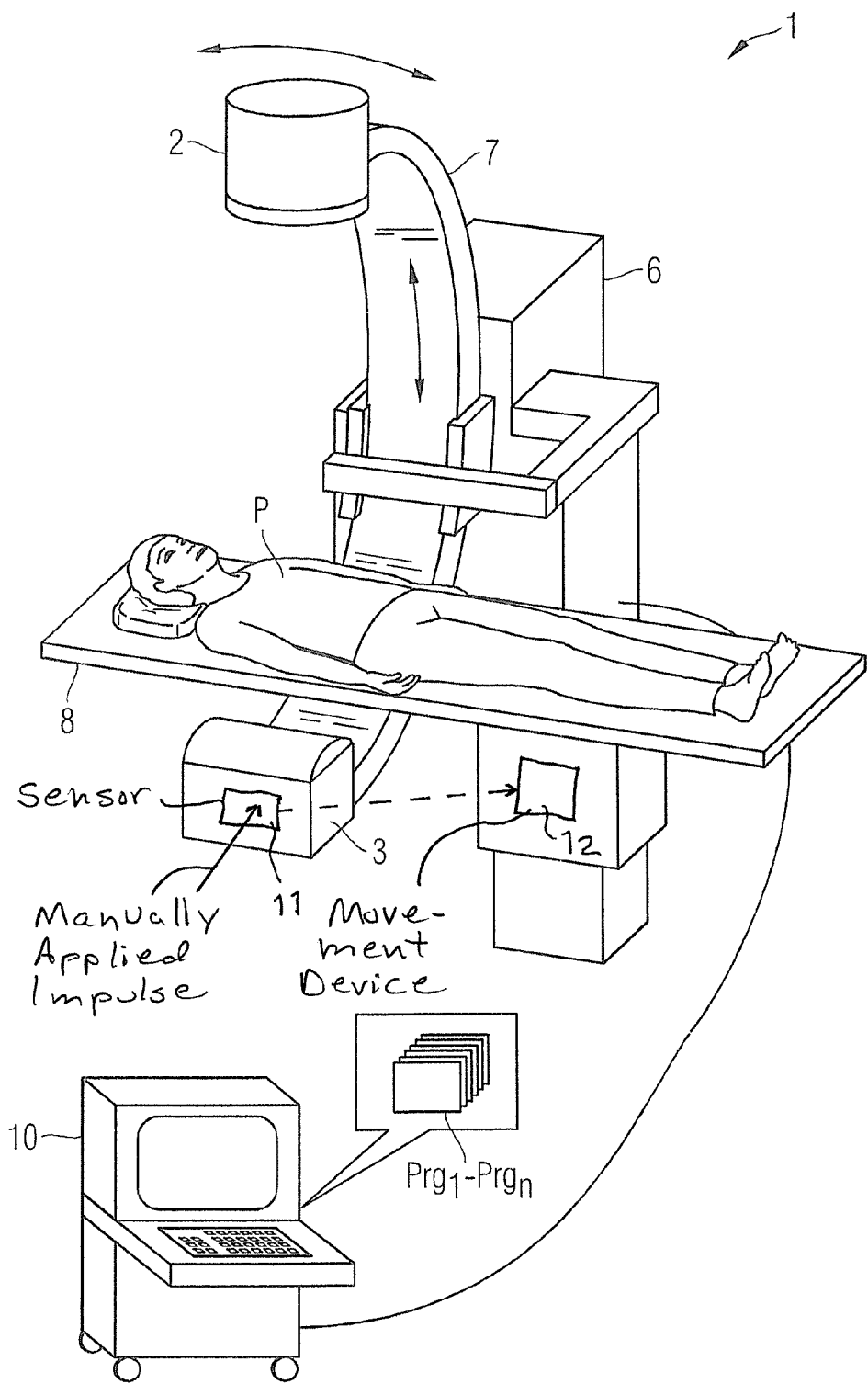
FIG. 6 is a schematic 3D representation of a C-arm system with control and computer system to implement the method according to the invention.

FIG. 6 also shows a conventional stationary C-arm system 1 which can likewise be operated according to the method according to the invention. The C-arm system 1 comprises a housing 6 with articulated C-arm thereupon, which C-arm has at its ends an x-ray tube 2 and a flat panel detector 3. The patient P to be examined is located on a patient bed 8. The control of the C-arm system (including the image processing) takes place via the connected control and computer system 10, which for this executes the programs $Prg_1$-$Prg_n$ stored in the memory. The method according to the invention is hereby also executed given the conventional C-arm system 1 (shown here in a schematic 3D representation).

As shown in FIG. 6, the C-arm 7 can be provided with a movement device 12 that has a sensor 11 that detects manual movement forces (impulses) at the C-arm 7 and, given selection of a predetermined movement mode, rotates in combination and linearly moves the C-arm 7 corresponding to the direction of the detected movement impulse, such that the focus is held stationary but a movement of the detector 3 takes place in the direction of the detected movement impulse.

Overall, a C-arm system and a method for image acquisition of a projective x-ray image with a C-arm system are thus proposed, wherein the projection region of the subject that is to be imaged is larger than the maximum projection region that is covered by a stationary beam, and to generate a complete exposure of the entire projection region to be imaged at least two projective individual exposures are created and combined, wherein the creation of the at least two individual exposures takes place given a focus that is stationary relative to the subject and given a modified solid angle.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating a two-dimensional x-ray projection image that is free of parallax error using a C-arm system comprising a C-arm on which an x-ray source and a radiation detector are mounted opposite each other, said x-ray source emitting, from a focus, an x-ray beam having a solid angle, said method comprising:

acquiring image data with said radiation detector from a projection region of a subject located between said x-ray source and said radiation detector, said projection region being larger than a maximum projection region covered by said solid angle of said x-ray beam when said x-ray beam is stationary, by irradiating the subject with said x-ray beam to acquire at least two individual projection exposures of the subject with said focus of said x-ray source being stationary relative to said subject and with said solid angle being modified respectively for acquiring said at least two individual exposures;

acquiring said image data in at least three individual exposures and by causing said C-arm, between said at least three individual exposures, to execute a first movement comprising a combined rotation around a middle point of said C-arm orthogonal to an orbital plane spanned by said C-arm and a translation orthogonal to said orbital plane, and a second movement comprising a combined rotation around said middle point of said C-arm in said orbital plane, and a translation in said orbital plane;

supplying said image data to a processor and, in said processor, generating a complete exposure of an entirety of said projection region from said at least two individual exposures, said complete exposure being free of parallax error due to said focus being stationary while acquiring the image data respectively for said at least two individual exposures; and in said processor, generating a data file representing said complete exposure and making said data file available at an output of said processor in electronic form.

2. A method as claimed in claim 1, further comprising acquiring said image data by moving said C-arm between said at least two individual exposures with a movement that causes said detector to be panned on a spherical surface having said stationary focus as a center.

3. A method as claimed in claim 1, further comprising acquiring said image data by moving said C-arm between said at least two individual exposures with a movement that causes said focus to always be located at a position, at least during acquisition of said image data that is stationary relative to said subject.

4. A method as claimed in claim 1, further comprising acquiring said image data by, between said at least two individual exposures, causing said C-arm to execute a combined rotation around a middle point of said C-arm in an orbital plane spanned by said C-arm, and a translation in said orbital plane.

5. A method as claimed in claim 1, further comprising acquiring said image data by, between said at least two individual exposures, causing said C-arm to execute a combined rotation around a middle point of said C-arm that is orthogonal to an orbital plane spanned by said C-arm, and a translation that is orthogonal to said orbital plane.

6. A method as claimed in claim 1, further comprising, in said processor, spatially transforming at least one of said at least two individual exposures when combining said at least two individual exposures to form said complete exposure, in order to cause said complete exposure to be in a common plane.

7. A method as claimed in claim 1, further comprising acquiring said image data by manually setting a position of said C-arm for a central projection, and acquiring a central individual exposure of said subject with said C-arm in said manually set position, as well as said at least two individual exposures, and generating said combined exposure from said central individual exposure and said at least two individual exposures.

8. A method as claimed in claim 7, further comprising manually setting a predetermined number of said at least two individual exposures, and automatically operating said C-arm and said x-ray source to acquire image data for said predetermined number of individual exposures.

9. A method as claimed in claim 8, further comprising setting said predetermined number of individual exposures to be eight individual exposures situated around said central projection.

10. A method for generating a two-dimensional x-ray projection image that is free of parallax error using a C-arm system comprising a C-arm on which an x-ray source and a radiation detector are mounted opposite each other, said x-ray source emitting, from a focus, an x-ray beam having a solid angle, said method comprising:

acquiring image data with said radiation detector from a projection region of a subject located between said x-ray source and said radiation detector, said projection region being larger than a maximum projection region covered by said solid angle of said x-ray beam when said x-ray beam is stationary, by irradiating the subject with said x-ray beam to acquire at least two individual projection exposures of the subject with said focus of said x-ray source being stationary relative to said subject and with said solid angle being modified respectively for acquiring said at least two individual exposures;

manually establishing said projection region by manually entering at least three vertices of said projection region into a computerized control unit that operates said C-arm, and automatically operating said C-arm from said control unit to acquire said image data for said at least two individual exposures according to said projection region having said at least three manually defined vertices;

acquiring said image data in at least three individual exposures and by causing said C-arm, between said at least three individual exposures, to execute a first movement comprising a combined rotation around a middle point of said C-arm orthogonal to an orbital plane spanned by said C-arm and a translation orthogonal to said orbital plane, and a second movement comprising a combined rotation around said middle point of said C-arm in said orbital plane, and a translation in said orbital plane;

supplying said image data to a processor and, in said processor, generating a complete exposure of an entirety of said projection region from said at least two individual exposures, said complete exposure being free of parallax error due to said focus being stationary while acquiring the image data respectively for said at least two individual exposures; and in said processor, generating a data file representing said complete exposure and making said data file available at an output of said processor in electronic form.

11. A method as claimed in claim 1, further comprising acquiring said image data for a central individual image and a plurality of portions of adjacent individual images that are adjacent to said central individual image, as said at least two individual images.

* * * * *